United States Patent
Gannon

[11] Patent Number: 6,140,929
[45] Date of Patent: Oct. 31, 2000

[54] SELF-TESTING GROUNDING DEVICE

[75] Inventor: Joseph R. Gannon, Chicago, Ill.

[73] Assignee: Lucent Technologies, Inc., Murray Hill, N.J.

[21] Appl. No.: 09/208,054

[22] Filed: Dec. 9, 1998

[51] Int. Cl.[7] .................................................. G08B 21/00
[52] U.S. Cl. ..................... 340/649; 340/650; 361/220; 324/510
[58] Field of Search .................... 340/649, 650, 340/652, 657; 361/212, 220; 324/509, 510, 457

[56] References Cited

U.S. PATENT DOCUMENTS

| | | | |
|---|---|---|---|
| 4,605,984 | 8/1986 | Fiedler . | |
| 4,638,399 | 1/1987 | Maroney et al. | 361/220 |
| 4,736,157 | 4/1988 | Betker et al. . | |
| 4,745,519 | 5/1988 | Breidegam . | |
| 5,461,369 | 10/1995 | Campbell et al. | 340/649 |
| 5,623,255 | 4/1997 | Yang | 340/649 |
| 5,686,897 | 11/1997 | Loh | 340/649 |
| 5,872,455 | 2/1999 | Pohribnij et al. | 324/509 |
| 5,952,931 | 9/1999 | Chotichanon et al. | 340/649 |

FOREIGN PATENT DOCUMENTS

0580913 A1  2/1994  European Pat. Off. .

*Primary Examiner*—Edward Lefkowitz
*Attorney, Agent, or Firm*—King and Schickli, PLLC

[57] ABSTRACT

A resistance tester is incorporated into a grounding device. The resistance tester includes a test circuit, a battery, a switch and a set of indicator devices. With the grounding device being worn and the cord end of the device in contact with the user so as to form a closed circuit, the test circuit measures the resistance level of the grounding device upon activation of the switch. The indicator devices provide a visual indication of the resistance level, i.e., too high, too low or within acceptable limits. The resistance tester is self-contained and may be used anytime by the user to ensure that the resistance of the grounding device is acceptable.

22 Claims, 3 Drawing Sheets

SELF-TESTING GROUNDING DEVICE

BACKGROUND OF THE INVENTION

The present invention relates in general to a grounding device, and, more particularly, to a self-testing grounding device having a resistance tester coupled directly to the device.

Static electricity provides problems in a number of industries, most particularly the electronics industries, with the advent of integrated circuits and other microelectronic components. Integrated circuits, for instance, may be disabled or destroyed by over-voltages or high power densities resulting from static electricity. Certain junctions in such circuits can be destroyed by as little as a 50-volt potential, which radically changes the doping structure in their lattices. High power densities resulting from excessive potential and imperfections in circuit layout or structure can vaporize or radically alter the silicon substrate and thus impair or destroy a circuit's performance. Yet a person walking on a carpet on a dry day can accumulate as much as 30,000 volts of potential, and can triboelectrically generate thousands of volts by simply changing position in a chair or handling a styrofoam cup.

A person can inadvertently discharge such static electric potential into a circuit or component by touching it and causing overvoltage or excessive power density. Additionally, the potential in such a person's body can induce a charge in a circuit that can later cause overvoltage or excessive power density when the circuit is subsequently grounded.

More and more frequently, therefore, manufacturers of integrated circuits and other similar microelectronic components are taking measures to limit the failure rate of those circuits and components by attempting to keep them as well as their environment at zero electrical potential. Such measures include providing workers and work stations with antistatic carpet, conductive or dissipative grounded desk top work surfaces, hot air ion generators which emit ions to neutralize static charges, and grounding devices to keep workers at zero potential. The term "conductive" herein, and according to its customary usage in the art, means an electrical resistance of between zero and $10^5$ ohms. Similarly, "dissipative" means a resistance of between $10^5$ and $10^9$ ohms, "antistatic" means a resistance of between $10^9$ and $10^{14}$ ohms, and "insulative" means a resistance of more than $10^{14}$ ohms.

A grounding device must have several features in order to perform its grounding function effectively. First, it must ensure that the user's skin is electrically connected to ground. This connection is typically accomplished by a conductive surface on the inside of a strap portion of the device contacting the skin. The conductive surface is electrically connected to a grounding cord which leads from the strap portion to a grounded electrical connection. If the electrical contacting surface on the inside of the strap portion becomes dirty or fouled by oil, perspiration or hair, the strap portion may lose its effectiveness. It is therefore important to form the conductive surface on the inner surface of the strap portion from a conductive material that does not easily become dirty or fouled.

Second, comfort is a premium consideration, because if the strap portion is uncomfortable, the wearer will be tempted to remove it and thereby defeat the grounding function possibly resulting in damage to electrical components on which the wearer is working. A strap portion that is easily stretchable, that breathes, that is attractive and that poses minimum inconvenience to the wearer is therefore highly desired. The situations in which grounding devices or straps are used heightens the importance of their being comfortable so that they are continuously worn and maintain continuous electrical contact with the skin.

Persons working on microelectronic components or integrated circuits may be completely unaware that minor static electrical charges have accumulated, and may therefore unknowingly be in a position to disable circuits. If the strap portion is loose or has been removed, the persons may be unaware that electrical discharges transmitted from their fingers are disabling these circuits. (A typical person cannot sense a static electrical discharge of less than approximately 3,500 volts.) Damage to the circuits may not be discovered until hours, days or weeks later, when the circuits have been placed in components or devices which fail in the field. Removal and repair or replacement of these circuits once in the field is far costlier than avoiding potential failure while the user is handling the circuits. Thus, the user's employer typically must depend upon the effectiveness of the grounding device to maintain a lower failure rate of such electronic circuits and components, by maintaining continuous electrical contact with the user's body.

Third, the proper resistance of the grounding device must be maintained to ensure the user's safety and the effectiveness of the device. The grounding resistance of a typical grounding device is approximately 1 megohm to limit the drain of electrostatic discharge (ESD) and to protect the user in the event of sudden discharge of current. The unrestricted flow of ESD through a "conductive" grounding device could actually damage an integrated circuit while the sudden discharge of current resulting from an electrical short could endanger the safety of the user. Similarly, a grounding device that has too much resistance may not drain charge fast enough which also could result in damage to an integrated circuit.

The user typically tests the resistance of the grounding device one or more times a day at a stand alone resistance tester. The tester is relatively expensive and is usually centrally located so that it may be used by a number of users. Typically, the cord end of the of the grounding device is plugged into the tester while the strap portion is being worn by the user. The tester then determines the resistance of the grounding device and provides an indication whether it is acceptable to continue using the device. Such a tester is inconvenient, and, since each and every user must make a conscious effort to go to the tester to test their grounding devices, its use may be intentionally or inadvertently neglected. Further, the resistance of the grounding device can change during use so that these inconvenient tests preferably are performed multiple times during continuing use of the grounding devices.

Accordingly, there is a need for a grounding device that includes a self-contained resistance tester. Preferably, such a device would be relatively inexpensive, easy to use, and easy to manufacture.

SUMMARY OF THE INVENTION

The present invention meets this need by providing a grounding device that includes a resistance tester that is incorporated into the grounding device. The resistance tester includes a test circuit, a battery, a switch and a set of indicator devices. With a strap portion of the grounding device being worn and the cord end of the device in contact with the user so as to form a closed circuit, the test circuit measures the resistance level of the grounding device upon activation of the switch. The indicator devices provide a visual indication of the resistance level, i.e., too high, too low or within acceptable limits. The resistance tester is self-contained and may be used anytime by the user to ensure that the resistance of the grounding device is acceptable.

According to a first aspect of the present invention, a self-testing grounding device comprises a strap for making a low resistance interface with a limb of a user of the grounding device and a predetermined resistance connection of the user to ground potential, and a resistance tester incorporated into the strap. The resistance tester provides an indication of a grounding resistance provided by the grounding device between the user and ground potential.

Preferably, the resistance tester provides a first indication if the grounding resistance generally corresponds to the predetermined resistance. The resistance tester may also provide a second indication if the grounding resistance is greater than the predetermined resistance and a third indication if the grounding resistance is less than the predetermined resistance. In one example of the present invention, the predetermined resistance is approximately 1 megohm and the tester provides the second indication if the grounding resistance is greater than approximately 10 megohms and the third indication if the grounding resistance is less than approximately 0.584 megohms.

The strap comprises a first portion that interfaces with the limb of the user and a cord portion extending from the first portion with the resistance tester preferably being incorporated into the cord portion. Alternatively, the resistance tester may be incorporated into the first portion of the strap. Preferably, the resistance tester comprises a test circuit, a battery, a switch and at least one indicator device. The test circuit is coupled in series with the battery and the switch while the indicator device is controlled by the test circuit. The indicator device preferably provides a visual indication of the grounding resistance. The indicator device may comprise a first indicator device, a second indicator device and a third indicator device, each of which may comprise a light emitting diode. The battery is preferably a lithium battery.

The test circuit may comprise a window comparator circuit having first and second outputs coupled to inputs of an AND-gate and an input receiving an input voltage corresponding to the grounding resistance of the grounding device. The first and second outputs are at a first logic level voltage if the input voltage is within a window of the window comparator circuit between a first voltage and a second voltage corresponding generally to acceptable extremes of the predetermined resistance, the first output being at a second logic level voltage if the input voltage is greater than the first voltage corresponding to a resistance greater than the predetermined resistance and the second output being at the second logic level voltage if the input voltage is less than the second voltage corresponding to a resistance less than the predetermined resistance. The window comparator circuit may comprise first and second op-amps while the AND-gate may comprise third and fourth op-amps. The first and second op-amps preferably comprise open collector outputs while the third and fourth op-amps preferably comprise interconnected open collector outputs. The predetermined resistance may be provided by a resistor positioned within the strap or the resistance tester itself.

According to another aspect of the present invention, a self-testing grounding device comprises a strap having a first portion that interfaces with a person's limb and a cord portion extending from the first portion. A resistance tester is mounted on either the first portion or the cord portion of the strap and comprises a test circuit, a battery, a switch, a first indicator device, a second indicator device and a third indicator device. The test circuit is coupled in series with the battery and the switch. The test circuit controls the first, second and third indicator devices and measures a grounding resistance of the grounding device upon activation of the switch with the first indicator device indicating that the grounding resistance generally corresponds to a predetermined resistance of the grounding device, the second indicator device indicating that the grounding resistance is greater than the predetermined resistance and the third indicator device indicating that the grounding resistance is less than the predetermined resistance.

According to yet another aspect of the present invention, a self-testing grounding device comprises a strap having a first portion that interfaces with a person's limb and a cord portion extending from the first portion. A resistance tester is incorporated into either the first portion or the cord portion of the strap and comprises a test circuit, a battery, a switch, a first indicator device, a second indicator device and a third indicator device. The test circuit is coupled in series with the battery and the switch. The test circuit controls the first, second and third indicator devices and measures a grounding resistance of the grounding device upon activation of the switch. The test circuit includes a window comparator circuit having first and second op-amps coupled to an AND-gate with the first and second op-amps receiving an input voltage corresponding to the grounding resistance of the grounding device. If the input voltage is between a first voltage and a second voltage corresponding generally to a predetermined resistance of the grounding device then a first logic level voltage results from the first and second op-amps and is input to the AND-gate thereby operating the first indicator device. If the input voltage is greater than the first voltage corresponding to a resistance greater than the predetermined resistance then a second logic level voltage is output from the first op-amp operating the second indicator device. If the voltage input is less than the second voltage corresponding to a resistance less than the predetermined resistance then the second logic level voltage is output from the second op-amp operating the third indicator device. The first logic level voltage corresponds to a logic one and the second logic level voltage corresponds to a logic zero.

Accordingly, it is an object of the present invention to provide a grounding device having a self-contained resistance tester to measure the resistance of the grounding device. It is another object of the present invention to provide such a grounding device that is relatively inexpensive, easy to use and easy to manufacture.

Other features and advantages of the invention will be apparent from the following description, the accompanying drawings and the appended claims.

DETAILED DESCRIPTION OF THE INVENTION

Figure 1:
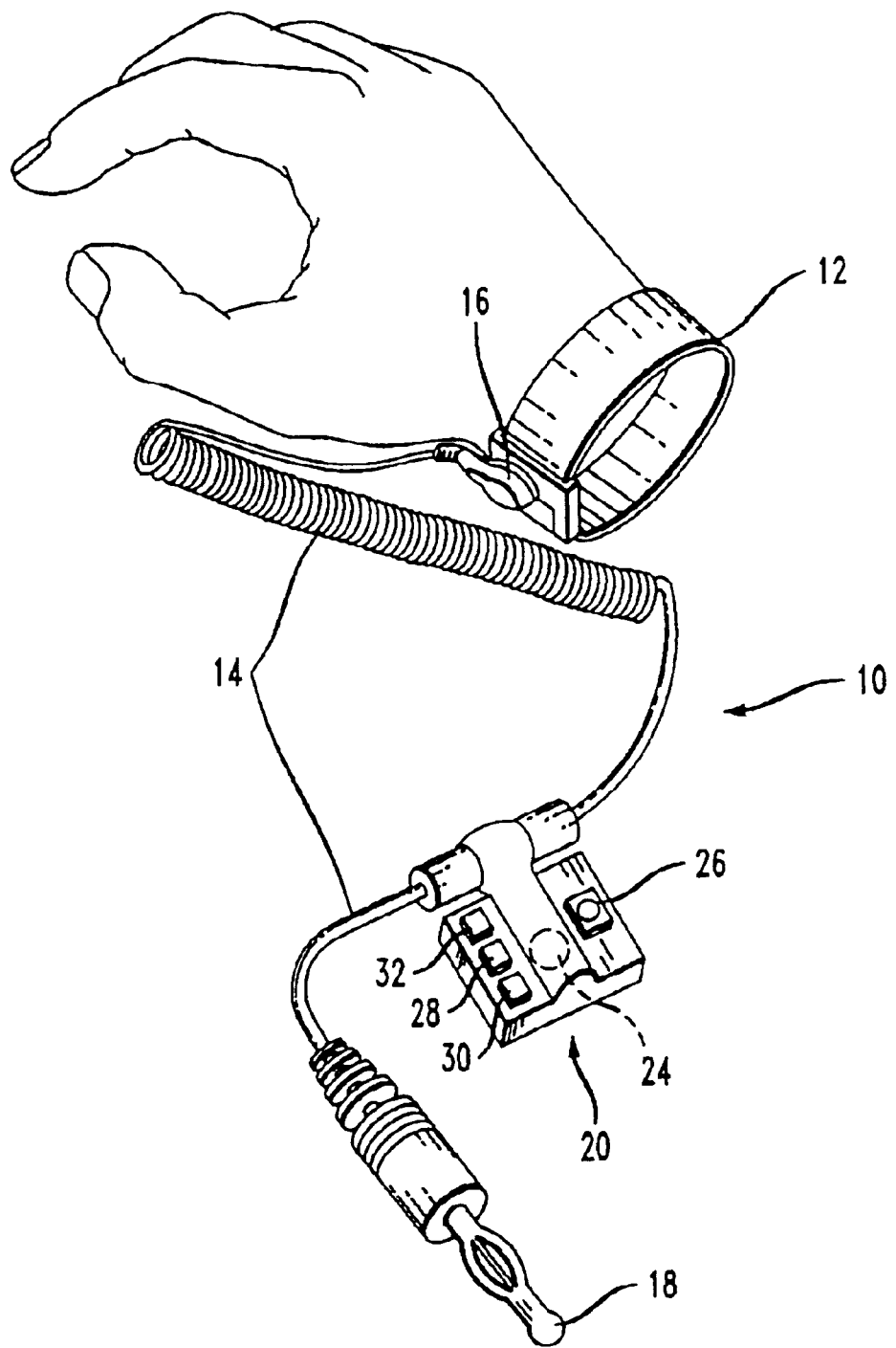
FIG. 1 is a perspective view of a grounding device according to the present invention having a resistance tester incorporated therein.

Referring now to FIG. 1, a grounding device 10 according to the present invention comprises a strap which includes a limb engaging first portion 12 and a cord portion 14 extending from the first portion 12. While the first portion 12 is shown electrically interfacing with a person's wrist, it will be appreciated by those skilled in the art that the first portion 12 may interface with other areas or limbs of the body, such as the ankle. The first portion 12 may have any desired configuration and may be formed of any suitable materials. One example of a desired configuration and suitable materials is disclosed in U.S. Pat. No. 4,577,256 which is incorporated herein by reference. The cord portion 14 interfaces with the first portion 12 via a snap connector 16 thereby allowing the cord portion 14 to be separated from the first portion 12 as desired. However, it will be appreciated by those skilled in the art that the cord portion 14 may be permanently coupled to the first portion 12 as desired.

The cord portion 14 includes a 1 megohm grounding resistor and a male connector 18 that interfaces with a corresponding female connector (not shown) of a grounding station (not shown) to carry electrostatic charges from the user's body to ground and to prevent electric shock if the grounding device 10 contacts a power source. The 1 megohm grounding resistance is incorporated into the snap connector 16 in the illustrated embodiment.

Figure 2:
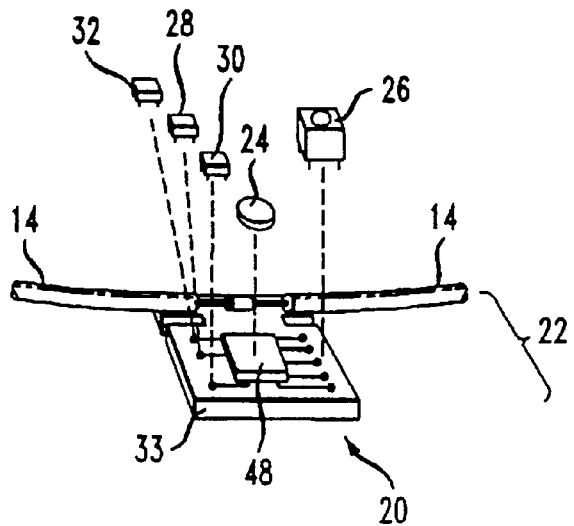
FIG. 2 is an exploded view of the resistance tester of FIG. 1.

In accordance with the invention of the present application, the grounding device 10 also includes a resistance tester 20. In the illustrated embodiment, the resistance tester 20 is incorporated into the cord portion 14 of the grounding device 10. Referring also to FIG. 2, the resistance tester 20 includes a test circuit 22, a battery 24 (see FIG. 3A), a switch 26 (see FIG. 3A), a first indicator device 28, a second indicator device 30 and a third indicator device 32 mounted on a printed circuit board 33. With the first portion 12 of the grounding device 10 interfacing with the skin of the user and the male connector 18 being held or otherwise contacting the skin of the user so as to form a closed loop, the test circuit 22 measures the grounding resistance of the grounding device 10 upon activation of the switch 26 and controls the indicator devices 28, 30 and 32 so as to provide an indication of the resistance of the grounding resistance. In the illustrated embodiment, the indicator devices 28, 30, 32 comprise different colored light emitting diodes (LEDs).

The first indicator device 28, a green LED, indicates a grounding resistance corresponding generally to acceptable extremes of the desired resistance of the grounding device 10, the second indicator device 30, a yellow LED, indicates a grounding resistance greater than the desired resistance of the grounding device 10, and the third indicator device 32, a red LED, indicates a grounding resistance less than the desired resistance. For the illustrated embodiment, the battery 24 comprises a 3.0 volt lithium button cell battery that powers the test circuit 22 as well as the indicator devices 28, 30, 32. It should be apparent that other types of batteries and voltage levels may be used in the invention of the present application.

Figure 3A:
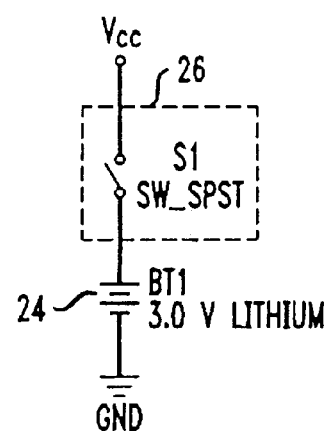
FIGS. 3, 3A and 3B form a schematic diagram of the resistance tester of FIG. 1.
Figure 3B:
Figure 3:
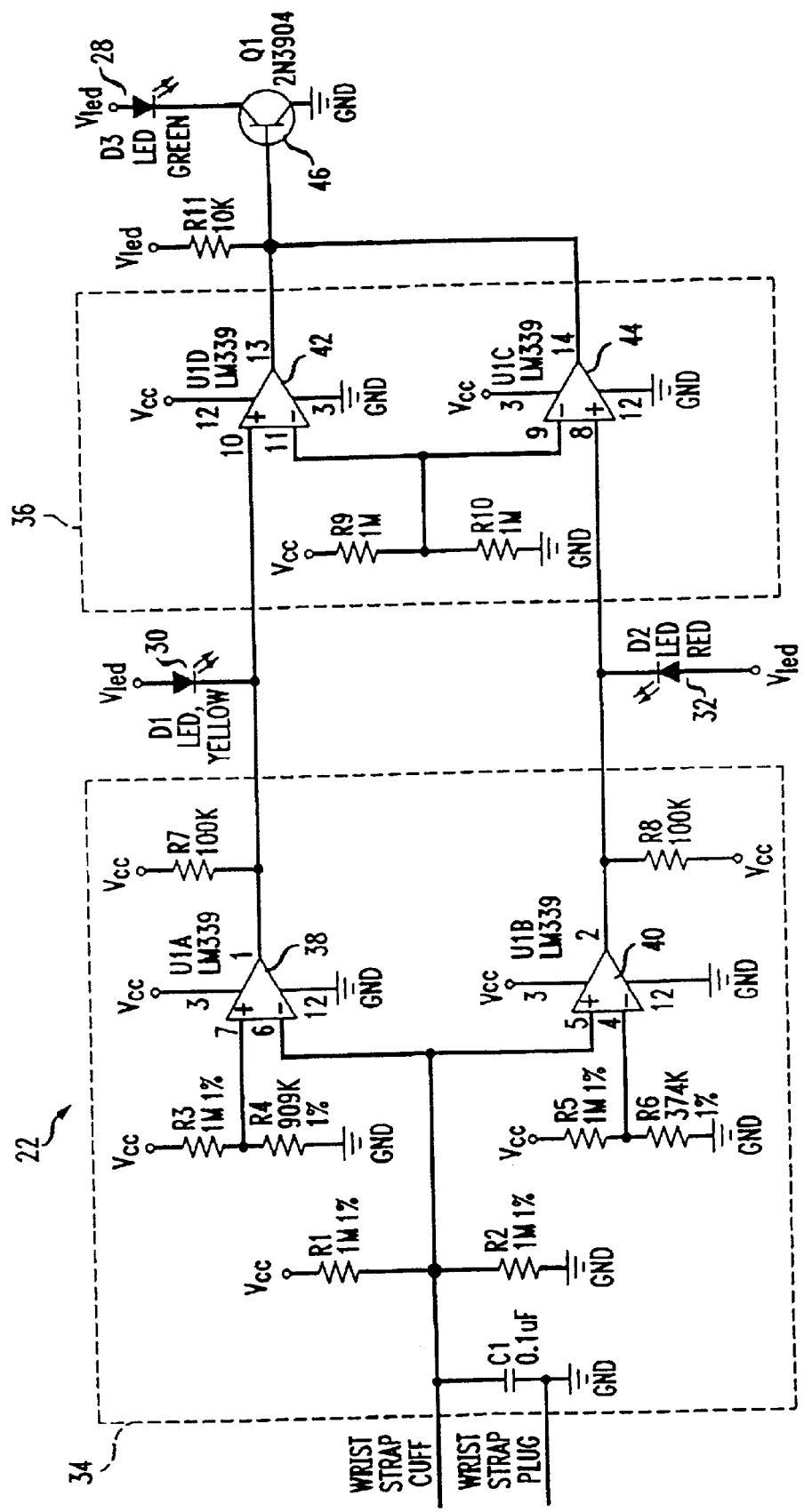

As shown in FIGS. 3, 3A and 3B, the test circuit 22 includes a window comparator 34 coupled to an AND-gate 36. The window comparator 34 comprises a first operational amplifier (op-amp) 38, a second op-amp 40 and a pair of series connected 1 megohm resistors R1, R2 with the resistance of the grounding device 10 being applied in parallel with the resistor R2 and a smoothing capacitor C1. The voltage resulting from the parallel combination of the grounding resistance of the grounding device 10 and the resistor R2 is input to the inverting input (−) of the first op-amp 38 and the non-inverting input (+) of the second op-amp 40. The non-inverting input of the first op-amp 38 receives a voltage of approximately 1.43 volts resulting from the series combination of resistors R3 and R4. The inverting input of the second op-amp 40 receives a voltage of approximately 0.81 volts resulting from the series combination of resistors R5 and R6.

The first and second op-amps 38, 40 provide open collector outputs such that their outputs would normally float when the input voltage to the window comparator 34 is within the window defined by the comparator 34, i.e., from around 0.81 volts to around 1.43 volts. However, the outputs of the first and second op-amps 38, 40 are not allowed to float but are pulled high to $V_{cc}$ or a first logic level voltage (logic level one) by pull-up resistors R7 and R8. Accordingly, if the voltage resulting from the grounding resistance of the grounding device is between 0.81 volts and 1.43 volts, the window of the window comparator 34 in the illustrated embodiment, the first and second op-amps 38, 40 in combination with the pull-up resistors R7, R8, generate outputs equal to the first logic level voltage, logic level one, to the AND-gate 36. Such a grounding resistance of the grounding device 10 corresponds generally to acceptable extremes of the desired resistance of the grounding device 10. Specifically, such a grounding resistance corresponds to acceptable extremes ranging from approximately 0.584 megohms to approximately 10.2 megohms in a working embodiment of the invention. With the outputs of the first and second op-amps 38, 40 pulled high, both the second and third indicator devices 30, 32 are turned off.

The outputs from the first and second op-amps 38, 40 are coupled to the non-inverting inputs (+) of a third op-amp 42 and a fourth op-amp 44, respectively, of the AND-gate 36. The inverting inputs (−) of the third and fourth op-amps 42, 44 receive a voltage of approximately 1.5 volts resulting from the series combination of resistors R9 and R10. Therefore, a voltage between 0.81 and 1.43 volts corresponding to the desired and acceptable grounding resistance of the grounding device 10 and voltage window of the window comparator 34, causes the first logic level voltage, logic level one, to be input into each non-inverting input of the third and fourth op-amps 42, 44. As both non-inverting inputs are greater than the respective inverting inputs, both outputs of the third and fourth op-amps 42, 44, which would otherwise float, are pulled high to the first logic level voltage by a pull-up resistor R11. This high voltage is applied to the base-emitter junction of an NPN transistor 46 thereby turning-on both transistor 46 and the first indicator device 28. Current through the first indicator device 28, as well as the second and third indicator devices 30, 32, is limited by a resistor R12 (see FIG. 3B). Accordingly, a grounding resistance resulting in a voltage within the window of the window comparator 34, causes the first indicator device 28 to turn-on and the second and third indicator devices 30, 32 to be turned off. The resistance tester 22 therefore provides an indication that the grounding resistance is within acceptable limits.

Conversely, if the voltage resulting from the grounding resistance of the grounding device 10 is greater than approximately 1.43 volts and outside of the window of the window comparator 34, the output of the first op-amp 38 is pulled to ground or a second logic level voltage (logic level zero) while the second op-amp 40 outputs the first logic level voltage. With the output of the first op-amp 38 pulled to ground, the second indicator device 30 turns on. The third indicator device 32 is off as the output of the second op-amp 40 is high. Further, a ground voltage is applied to the non-inverting input of the third op-amp 42 thereby causing the output of the third op-amp 42 to be pulled to ground. With the output of the third op-amp 42 pulled to ground, the transistor 46 is turned off along with the first indicator device 28. It should be apparent that the state of the fourth op-amp 44 is irrelevant once the output of the third op-amp 42 is pulled to ground. Accordingly, a grounding resistance resulting in a voltage greater than approximately 1.43 volts causes the second indicator device 30 to turn-on and the first and third indicator devices 28, 32 to be turned off. The resistance tester 22 therefore provides an indication that the grounding resistance is too high.

If the voltage resulting from the grounding resistance of the grounding device 10 is less than approximately 0.81 volts and outside of the window of the window comparator 34, the output of the second op-amp 40 is pulled to ground or the second logic level voltage while the first op-amp 38 outputs the first logic level voltage. With the second op-amp 40 pulled to ground, the third indicator device 32 is turned on. The second indicator device 30 is off as the output of the first op-amp 38 is high. Further, a ground voltage is applied to the non-inverting input of the fourth op-amp 44 thereby causing the output of the fourth op-amp 44 to be pulled to ground. With the output of the fourth op-amp 44 pulled to ground, the transistor 46 is turned off along with the first indicator device 28. It should be apparent that when the output of either of the third or fourth op-amps 42, 44 is pulled to ground, the output of the other op-amp is irrelevant. Accordingly, a grounding resistance resulting in a voltage less than approximately 0.81 volts causes the third indicator device 32 to be turned on and the first and second indicator devices 28, 30 to be turned off. The resistance tester 22 therefore provides an indication that the grounding resistance is too low.

With the resistance tester 20 self-contained in the grounding device 10, the grounding resistance of the grounding device 10 may be tested directly as many times as desired without the wearer having to waste time by interfacing with a relatively expensive and separate, stand alone tester. The grounding device 10 may therefore be tested directly at each workstation or anytime the wearer moves from one area to another to ensure that the grounding resistance is acceptable. The ease of the test may encourage more frequent testing to ensure that the grounding device 10 is functioning as intended throughout the day.

Further, it should be apparent that the resistance tester 20 adds an extra measure of safety as the 1 megohm resistance of the resistor R2 forms part of the grounding resistance of the grounding device 10 as the resistor R2 is in series with the 1 megohm grounding resistor built into the snap connector 16 of the grounding device 10. It will therefore be appreciated by those skilled in the art that the present invention may be utilized with a grounding device that does not include a built-in resistor as the grounding resistance may be provided entirely by the resistance tester 20 itself.

In such a configuration, the resistance values of resistors R1, R2, R3, R4, R5 and R6 would have to be adjusted is apparent. With the grounding resistance provided by an 1 megohm resistor in the resistance tester 20, the skin and body resistance of the user will not be a factor in the measurement of the grounding resistance of the grounding device 10. While it is intended that the grounding resistance of the grounding device 10 be tested while the user is wearing the grounding device 10, the grounding resistance of the grounding device 10 may be measured without the user having to wear the grounding device 10.

The op-amps 38, 40, 42, and 44 form part of a single quad-op-amp chip 48 as shown in FIG. 2. However, it will be appreciated by those skilled in the art that the op-amps 38, 40, 42, 44 may comprise separate and distinct op-amp packages. It will be further appreciated by those skilled in the art that the resistance values of resistors R1, R2, R3, R4, R5 and R6 may be adjusted as desired to change the window of the window comparator 34 and thus the high and low values for an acceptable grounding resistance of the grounding device 10. It will be even further appreciated by those skilled in the art that other indicator devices, not limited to visual devices, may be used to provide an indication of the grounding resistance of the grounding device 10. It should be apparent that the resistance tester 22 may be incorporated into the first portion 12 of the grounding device 10 if desired.

Having described the invention in detail and by reference to preferred embodiments thereof, it will be apparent that modifications and variations are possible without departing from the scope of the invention defined in the appended claims.

What is claimed is:

1. A self-testing grounding device comprising:
   a strap for making a low resistance interface with a limb of a user of said grounding device and a predetermined resistance connection of said user to ground potential, said strap comprising a first portion that interfaces with said limb of said user and a cord portion extending from said first portion to around potential; and
   a resistance tester incorporated into said cord portion of said strap and providing a first indication if said grounding resistance generally corresponds to said predetermined resistance, a second indication if said grounding resistance is greater than said predetermined resistance and a third indication if said grounding resistance is less than said predetermined resistance.

2. The self-testing grounding device of claim 1, wherein said predetermined resistance is approximately 1 megohm and wherein said tester provides said second indication if said grounding resistance is greater than approximately 10 megohms and said third indication if said grounding resistance is less than approximately 0.584 megohms.

3. The self-testing grounding device of claim 2, wherein said tester provides said first indication if said grounding resistance ranges from approximately 0.584 megohms to approximately 10 megohms.

4. The self-testing grounding device of claim 1, wherein said resistance tester comprises a test circuit, a battery, a switch and at least one indicator device, said test circuit being coupled in series with said battery and said switch, said at least one indicator device being controlled by said test circuit.

5. The self-testing grounding device of claim 4 wherein said at least one indicator device provides a visual indication of said grounding resistance.

6. The self-testing grounding device of claim 4, wherein said at least one indicator device comprises a first indicator device, a second indicator device and a third indicator device.

7. The self-testing grounding device of claim 6, wherein each of said first indicator device, said second indicator device and said third indicator device comprises a light emitting diode.

8. The self-testing grounding device of claim 4, wherein said battery is a lithium battery.

9. The self-testing grounding device of claim 4, wherein said test circuit comprises a window comparator circuit having first and second outputs coupled to inputs of an AND-gate and an input receiving an input voltage corresponding to said grounding resistance of said grounding device, said first and second outputs being at a first logic level voltage if said input voltage is within a window of said window comparator circuit between a first voltage and a second voltage corresponding generally to acceptable extremes of said predetermined resistance, said first output being at a second logic level voltage if said input voltage is greater than said first voltage corresponding to a resistance greater than said predetermined resistance and said second output being at said second logic level voltage if said input voltage is less than said second voltage corresponding to a resistance less than said predetermined resistance.

10. The self-testing grounding device of claim 9, wherein said window comparator circuit comprises first and second op-amps.

11. The self-testing grounding device of claim 9, wherein said AND-gate comprises third and fourth op-amps.

12. The self-testing grounding device of claim 10, wherein said first and second op-amps comprise open collector outputs.

13. The self-testing grounding device of claim 11, wherein said third and fourth op-amps comprise interconnected open collector outputs.

14. The self-testing grounding device of claim 1, wherein said predetermined resistance is provided by a resistor positioned within said resistance tester.

15. A self-testing grounding device comprising:
a strap having a first portion that interfaces with a person's limb and a cord portion extending from said first portion; and
a resistance tester mounted on said cord portion of said strap, said resistance tester comprising a test circuit, a battery, a switch, a first indicator device, a second indicator device and a third indicator device, said test circuit being coupled in series with said battery and said switch, said test circuit controlling said first, second and third indicator devices and measuring a grounding resistance of said grounding device upon activation of said switch with said first indicator device indicating that said grounding resistance generally corresponds to a predetermined resistance of said grounding device, said second indicator device indicating that said grounding resistance is greater than said predetermined resistance and said third indicator device indicating that said grounding resistance is less than said predetermined resistance.

16. The self-testing grounding device of claim 15, wherein said predetermined resistance is provided by a resistor positioned within one of said first portion and said cord portion of said strap.

17. The self-testing grounding device of claim 15, wherein said predetermined resistance is provided by a resistor positioned within said resistance tester.

18. A self-testing grounding device comprising:
a strap having a first portion that interfaces with a person's limb and a cord portion extending from said first portion; and
a resistance tester incorporated into said cord portion of said strap, said resistance tester comprising a test circuit, a battery, a switch, a first indicator device, a second indicator device and a third indicator device, said test circuit being coupled in series with said battery and said switch, said test circuit controlling said first, second and third indicator devices and measuring a grounding resistance of said grounding device upon activation of said switch, said test circuit comprising a window comparator circuit having first and second op-amps coupled to an AND-gate, said first and second op-amps receiving an input voltage corresponding to said grounding resistance of said grounding device, a first logic level voltage resulting from said first and second op-amps being input to said AND-gate thereby operating said first indicator device if said input voltage is between a first voltage and a second voltage corresponding generally to a predetermined resistance of said grounding device, a second logic level voltage resulting from said first op-amp operating said second indicator device if said input voltage is greater than said first voltage corresponding to a resistance greater than said predetermined resistance, and said second logic level voltage resulting from said second op-amp operating said third indicator device if said voltage input is less than said second voltage corresponding to a resistance less than said predetermined resistance.

19. The self-testing grounding device of claim 18, wherein said first logic level voltage corresponds to a logic one.

20. The self-testing grounding device of claim 18, wherein said second logic level voltage corresponds to a logic zero.

21. The self-testing grounding device of claim 18, wherein said predetermined resistance is provided by a resistor positioned within one of said first portion and said cord portion of said strap.

22. The self-testing grounding device of claim 18, wherein said predetermined resistance is provided by a resistor positioned within said resistance tester.

* * * * *

UNITED STATES PATENT AND TRADEMARK OFFICE
CERTIFICATE OF CORRECTION

PATENT NO. : 6,140,929                       Page 1 of 1
DATED : October 31, 2000
INVENTOR(S) : Joseph R. Gannon It is certified that error appears in the above-identified patent and that said Letters Patent is hereby corrected as shown below:

<u>Column 8, claim 1,</u>
Line 25, "around" should read -- ground --.

Signed and Sealed this

Twelfth Day of February, 2002

Attest:

Attesting Officer

JAMES E. ROGAN
Director of the United States Patent and Trademark Office